United States Patent [19]

Bird et al.

[11] Patent Number: 6,147,260
[45] Date of Patent: Nov. 14, 2000

[54] PREPARATION OF 5-(3-BUTYRYL-2,4,6-TRIMETHYL)-2-(1-(ETHOXYIMINO) PROPYL)-3-HYDROXYCYCLOHEX-2-EN-1-ONE

[75] Inventors: Graham John Bird, Balwyn; Keith Geoffrey Watson, Surrey Hills, both of Australia

[73] Assignee: Orica Australia PTY, LTD, Victoria, Australia

[21] Appl. No.: 09/230,678

[22] PCT Filed: Jul. 25, 1997

[86] PCT No.: PCT/AU97/00471

§ 371 Date: Jun. 21, 1999

§ 102(e) Date: Jun. 21, 1999

[87] PCT Pub. No.: WO98/04510

PCT Pub. Date: Feb. 5, 1998

[30] Foreign Application Priority Data

Jul. 30, 1996 [AU] Australia ...................................... 1322

[51] Int. Cl.[7] .................. C07C 249/04; C07C 45/46; C07C 249/08

[52] U.S. Cl. ................ 564/256; 568/315; 568/337
[58] Field of Search ..................... 564/256; 568/315, 568/337

[56] References Cited

FOREIGN PATENT DOCUMENTS

| 34225/84 | 5/1985 | Australia . |
|---|---|---|
| 0 488 645 A1 | 6/1992 | European Pat. Off. . |
| 0 085 529 A2 | 8/1992 | European Pat. Off. . |
| WO 92/21649 | 12/1992 | WIPO . |

*Primary Examiner*—Peter O'Sullivan
*Attorney, Agent, or Firm*—Knobbe, Martens, Olson & Bear LLP

[57] ABSTRACT

A process of preparing the compound of formula (I) which comprises: (a) reacting butyryl chloride with the compound of formula (IV) in the presence of a Friedel-Crafts catalyst in an inert diluent to produce a compound of formula (II) and (b) reacting the compound of formula (II) with ethoxyamine. Compound (II) is also claimed.

8 Claims, No Drawings

PREPARATION OF 5-(3-BUTYRYL-2,4,6-TRIMETHYL)-2-(1-(ETHOXYIMINO) PROPYL)-3-HYDROXYCYCLOHEX-2-EN-1-ONE

This invention relates to a chemical process.

European Patent No. 85529 discloses a class of 2-[1-(alkoxyimino)-alkyl]-5-(substituted phenyl) cyclohexane-1,3-dione derivatives useful as selective herbicides.

A compound of this class, 5-(3-butyryl-2,4,6-trimethylphenyl)-2-[1-(ethoxyimino)propyl]-3-hydroxycyclohex-2-en-1-one, having the structural formula (1), has been found to be particularly useful in the selective control of graminaceous weeds.

European Patent No. 85529 describes the preparation of compounds of this type (although the compound of formula (I) is not itself disclosed).

PCT Appplication No WO 92/21649 discloses a process for making the compound of formula (I) by the reaction of butyryl chloride with a compound of formula (III).

The present invention provides an alternative process for preparation of the compound of formula (I).

According to the present invention, therefore, there is provided a process of preparing a compound of formula (I) which comprises reacting a compound of formula (IV) with butyryl chloride in the presence of a Friedel-Crafts reaction catalyst, in an inert diluent to produce a compound of formula (II) and reacting the compound of formula (II) with ethoxyamine. Suitable Friedel-Crafts catalysts include aluminium chloride, ferric chloride and mixtures of aluminium chloride and ferric chloride. Preferably the Friedel-Crafts catalyst is anhydrous aluminium chloride. The Friedel-Crafts catalyst is used in an amount of from 1 to 10 molar proportions with respect to the compound of formula (IV), and preferably from 3 to 5 molar proportions. The butyryl chloride is used in an amount of from 1 to 10 molar proportions and preferably from 1.5 to 2.5 molar proportions with respect to the compound of formula (IV).

The diluent used in the reaction of the compound of formula (IV) with butyryl chloride may be selected from those diluents known to be used in Friedel-Crafts reactions. It may for example be a hydrocarbon or a chlorinated hydrocarbon, or a nitro-hydrocarbon. Examples of suitable aliphatic and alicyclic hydrocarbons include the mixture of aliphatic hydrocarbons sold under the trade name Isopar M, which has a boiling range of 210–250° C., n-pentane, n-heptane, n-hexane, cycloheptane and cyclohexane. Chlorinated hydrocarbons include, for example, dichloromethane and tetrachloroethylene.

Nitro-hydrocarbons include, for example, nitrobenzene and nitromethane.

The reaction is preferably carried out at a temperature in the range from –10 to 100° C. and more preferably in the range 10 to 50° C.

In the reaction of the compound of formula (II) with ethoxyamine, the ethoxyamine is used in an amount of from 0.5 to 5 molar proportions with respect to the compound of formula (II), and preferably from 1.0 to 2.0 molar proportions.

The reaction is preferably carried out at a temperature in the range from 0 to 80° C. and more preferably in the range 20 to 50° C.

The reaction is suitably carried out in a solvent such as 2-propanol, cyclohexane, n-heptane, n-octane, or an aromatic hydrocarbon such as xylene or toluene.

Preferred solvents are n-heptane or 2-propanol.

The reaction may also be carried out in the presence of a catalyst. Suitable catalyst includes organo-tin compounds such as dibutyltin diacetate.

The order of addition of the reactants may be varied as required. For example the butyryl chloride may be added to the compound of formula (IV) and the Friedel Crafts catalyst in a solvent, or the butyryl chloride may be added to a slurry of the Friedel Crafts catalyst followed by addition of the compound of formula (IV) as a solution.

The compound 5-(3-butyryl-2,4,6-trimethylphenyl)-3-hydroxy-2-propionylcyclohex-2-en-1-one having the structural formula (II) is novel and as such forms a further aspect of the invention.

The compound of formula (IV), 3-hydroxy-2-propionyl-5-(2,4,6-trimethylphenyl)cyclohex-2-en-1-one is a known compound.

It is has surprisingly been found that performing the Friedel Crafts reaction before the oximation reaction greatly increases the productivity of the process for producing the compound of formula (I). Whereas the Friedel Crafts reaction described in PCT Application No. W092/21649 required up to 16 hours to reach completion, the Friedel-Crafts reaction to produce compounds of formula (II) in the present invention is complete in only 0.25 to 4 hours.

If desired, the compound (I) produced by the above process although of high quality, may be further purified by crystallisation from an anhydrous solvent. Such crystallisation has been described in European Patent Application No. 488645. Preferred solvents for crystallising the compound (I) in the anhydrous form include low-boiling (e.g. up to a maximum boiling-point of 100° C.) hydrocarbons for example, cyclohexane, hexane, heptane, and mixed hydrocarbons. The compound (I) is dissolved by warming in the anhydrous solvent to a maximum temperature of less than 80° C., and then cooled, when the anhydrous crystalline form of compound (I) separates and is filtered off and dried under vacuum. Generally, it is preferred to prepare the anhydrous crystalline form of compound (I), since it is easier to formulate into herbicidal compositions, and is more convenient to handle and transport. If desired, however, compound (I) can be obtained in the form of its crystalline monohydrate, by crystallising the compound (I) obtained by the process of the invention from a solvent containing a hydroxy group, for example a lower alkanol, containing a small proportion of water. The crystalline form of compound (I) so obtained is the mono-hydrate, with a melting point of 30° C.; this may be dried in air.

The invention is illustrated by the following Examples:

EXAMPLE 1

This Example illustrates the production of the compound of formula (II) using the Bouveault addition method.

Compound (IV), as a dry powder (28.6 g. 100% wt., 0.1 mol) was dissolved in tetrachloroethylene (145 ml ) at ambient temperature. Aluminium chloride (53.3 g, 100% wt., 0.4 mol) was added in portions over 15 minutes, controlling the temperature at 20–25° C. (exothermic) and the mixture was stirred for 15 minutes. n-Butyryl chloride (21.3 g, 100% wt., 0.2 mol) was added over a period of 30 minutes, maintaining the temperature at 20–25° C. (exothermic). The reaction mixture was stirred at 20–25° C. for 1 hour. The product slurry was drowned out into water (190 g) and 36% hydrochloric acid (86 g) while controlling the temperature between 40 and 45° C. The hydrolysis mixture was stirred for a further 30 minutes, allowed to settle and the phases separated. The tetrachloroethylene layer was washed twice at 40–45° C., once with water (150 g) and then by 10% sodium bicarbonate solution (125 g) and the phases separated after each wash. The tetrachloroethylene was removed by vacuum distillation (50 mmHg) at a batch temperature of 45–50° C. A steady stream of nitrogen was passed through the solution towards the end of the distillation to aid removal of the last traces of tetrachloroethylene. Yield of compound (II) was 32.0 g (89.9%).

The following Table gives results obtained by carrying out the above procedure under various reaction conditions and/or using various solvents.

TABLE 1

| Solvent | Reaction concentration [% w/w based on Cpd (IV)] | Molar Ratio [Compound (IV) = 1.0] AlCl$_3$ | Butyryl chloride | Temp./ ° C. | Addition Time/mins | Reaction Time/hrs | % Conversion to Compound (II) |
|---|---|---|---|---|---|---|---|
| Dichloromethane | 13 | 4.0 | 2.0 | 30 | 15 | 0.75 | 100 |
| Tetrachloroethylene | 11 | 4.0 | 2.0 | 50 | 15 | 0.5 | 99 |
| Tetrachloroethylene | 8.5 | 4.0 | 2.0 | 25 | 45 | 2 | 98 |
| Tetrachloroethylene | 8.5 | 3.5 | 2.0 | 45 | 60 | 1 | 98 |
| Tetrachloroethylene | 8.5 | 4.0 | 2.0 | 20 | 60 | 3 | 97 |
| Nitrobenzene | 9.0 | 4.0 | 2.0 | 20 | 60 | 2.5 | 93 |
| Cyclohexane | 16 | 3.5 | 1.25 | 20 | 10 | 3 | 50 |
| N-hexane | 24 | 4.0 | 2.0 | 50 | 30 | 4 | 61 |
| N-pentane | 24 | 4.0 | 2.0 | 25 | 15 | 4 | 97 |
| Cyclopentane | 24 | 4.0 | 2.0 | 35 | 15 | 2 | 89 |

EXAMPLE 2

This Example illustrates the production of the compound of formula (II) using Bouveault addition method.

Compound (IV), as a dry powder (28.6 g, 100% wt., 0.1 mol) was dissolved in nitrobenzene (145 ml) at ambient temperature. Ferric chloride (48.7 g, 100% wt., 0.3 mol) was added in portions over 15 minutes, controlling the temperature at 20–25° C. (exothermic) and the mixture was stirred for 15 minutes. n-Butyryl chloride (21.3 g, 100% wt., 0.2 mol) was added over a period of 30 minutes maintaining the temperature at 20–25° C. (exothermic). The reaction mixture was stirred at 20–25° C. for 1 hour. The product slurry was drowned out into water (190 g) and 36% hydrochloric acid (86 g) while controlling the temperature between 55 and 60° C. The hydrolysis mixture was stirred for a further 30 minutes, allowed to settle and the phases separated. The nitrobenzene layer was washed twice with water (2×150 g) at 55–60° C., the phases separated after each wash.

The following Table 2 gives results for carrying out the above procedure under various reaction conditions and/or using various solvents.

EXAMPLE 3

This Example illustrates the production of the compound of formula (II) using the Perrier addition method.

Aluminium chloride (46.7 g, 100% wt., 0.35 mol) was slurried in dichloromethane (90 ml) at ambient temperature. n-Butyryl chloride (13.3 g, 100% wt., 0.125 mol) was added over 10 minutes, controlling the reaction temperature at 18–22° C. (exothermic) and the mixture stirred for 30 minutes. A solution of Compound (IV) (28.6 g, 100% wt., 0.1 mol) in dichloromethane (40 ml) was added over 1 hour maintaining the reaction temperature at 20–25° C. (exothermic). The reaction mixture was stirred at 20–25° C. for 2 hours. The slurry was transferred slowly into a mixture of water (190 g) and 36% hydrochloric acid (86 g) controlling the hydrolysis temperature at 20–30° C. (exothermic). The hydrolysis mixture was stirred for a further 30 minutes, allowed to settle and the phases separated. The dichloromethane layer was washed twice with water (2×150g) at 25–30° C., the phases separated after each wash. The dichloromethane was removed by atmospheric distillation at a batch temperature of 30–35° C. Yield of compound (II) was 33.7 g (94.9%).

The following Table 3 gives results obtained by carrying out the above procedure under various reaction conditions and/or using various solvents.

TABLE 2

| Solvent | Reaction concentration [% w/w based on Cpd (IV)] | Molar Ratio [Compound (IV) = 1.0] FeCl$_3$ | Butyryl chloride | Temp./ ° C. | Addition Time/mins | Reaction Time/hrs | % Conversion to Compound (II) |
|---|---|---|---|---|---|---|---|
| Nitrobenzene | 14.5 | 3.0 | 2.0 | 20 | 15 | 1 | 90 |
| Nitrobenzene | 14.5 | 3.0 | 1.15 | 20 | 15 | 3 | 37 |
| Nitrobenzene | 14.5 | 4.0 | 2.0 | 20 | 15 | 0.75 | 99 |
| Nitrobenzene | 20 | 4.0 | 2.0 | 20 | 15 | 1 | 99.5 |
| Nitrobenzene | 23 | 4.0 | 2.0 | 20 | 15 | 0.25 | 95 |
| N-heptane | 14.5 | 4.0 | 2.0 | 20 | 60 | 1 | 50 |

TABLE 3

| Solvent | Reaction concentration [% w/w based on Cpd (IV)] | Molar Ratio [Compound (IV) = 1.0] AlCl₃ | Butyryl chloride | Temp. °C. | Addition Time [of Cpd (IV)]/mins | Reaction Time/hrs | % Conversion to Compound (II) |
|---|---|---|---|---|---|---|---|
| Dichloromethane | 13 | 3.5 | 1.25 | 20 | 30 | 2 | 90 |
| Dichloromethane | 13 | 3.5 | 1.2 | 20 | 30 | 0.5 | 99 |
| Nitromethane | | 3.5 | 1.25 | 20 | 30 | 2 | 60 |

EXAMPLE 4

This Example illustrates the production of the compound of formula (I).

Compound (II), as a solid (35.6 g, 100% wt., 0.1 mol) was slurred with n-heptane (119 ml) at 40–45° C. A solution of 50% aqueous ethoxyamine (7.9 g, 100% wt., 0.13 mol) was added over 1 hour maintaining the temperature at 40–45° C. The reaction mixture was stirred at 40–45° C. for 4 hours. Water was removed by vacuum distillation (100 mmHg) at a batch temperature of 47–50° C. using apparatus set-up to return n-heptane co-distillates to the batch. Azeotropic drying of the product solution was complete when all solids had dissolved. Batch volume was adjusted to 110 ml by adding dry n-heptane (20–30 ml). Anhydrous product was crystallised by step-wise cooling to 5° C. over 6 hours (1 hour at 40° C., 2 hours at 30° C., 1 hour at 20° C. and 2 hours at 5° C.). Yield of compound (I) was 31.6 g.

The following Table 4 gives results for carrying out the above procedure under various reaction conditions.

50% aqueous ethoxyamine (7.9 g, 100% wt., 0.13 mol) was added over 1 hour maintaining the temperature at 40–45° C. The reaction mixture was stirred at 40–45° C. for 4 hours before cooling to 10–15° C. The resultant precipitate (monohydrate form of the product) was isolated by filtration and the filter cake was washed with 2-propanol (20 ml) followed by water 2×35 ml). The monohydrate solid was slurried with dry n-heptane (250 ml) and the slurry dried by azeotropic vacuum distillation (100 mmHg) at a batch temperature of 47–50° C. Azeotropic drying of the product solution is complete when all solids have dissolved. Batch volume was adjusted to 100 ml by adding dry n-heptane (20–30 ml). Anhydrous product was crystallised by step-wise cooling to 5° C. over 6 hours (1 hour at 40° C., 2 hours at 30° C., 1 hour at 20° C. and 2 hours at 5° C. Yield of compound (I) was 27.5 g.

The following Table 5 gives results obtained by carrying out the above procedure using different solvents.

TABLE 4

| Solvent | Reaction concentration [% w/w based on Cpd (II)] | Molar Ratios [Compound (II) = 1.0] Ethoxyamine | Temp./° C. | Reaction Time/hrs | % Conversion to Compound (I) |
|---|---|---|---|---|---|
| N-heptane | 30 | 1.3 | 25 | 4 | 99.5 |
| N-heptane | 30 | 1.3 | 43 | 3 | 97 |
| N-heptane | 37 | 1.3 | 45 | 2 | 97 |
| Tetrachloroethylene | 16 | 1.3 | 42 | 4 | 99 |

EXAMPLE 5

This Example illustrates the production of the compound of formula (I).

Compound (II), as a solid 35.6 g, 100% wt. 0.1 mol) was dissolved in 2-propanol (63 ml) at 40–45° C. A solution of

TABLE 5

| Solvent | Reaction concentration [% w/w based on Cpd (II)] | Molar Ratios [Compound (II) = 1.0] Ethoxyamine | Temp./° C. | Reaction Time/hrs | % Conversion to Compound (I) |
|---|---|---|---|---|---|
| 2-Propanol | 42 | 1.3 | 38 | 3 | 99 |
| Cyclohexane | 28 | 1.3 | 40 | 4 | 97 |
| N-heptane | 30 | 1.3 | 40 | 4 | 92 |

(CHEMICAL FORMULA) IN DESCRIPTION

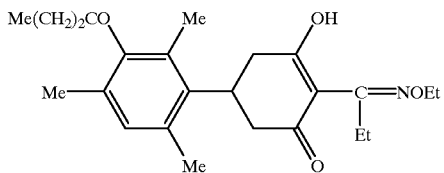
(I)

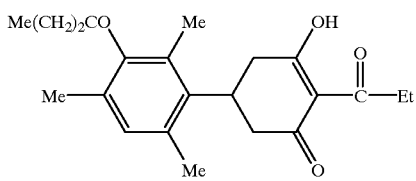
(II)

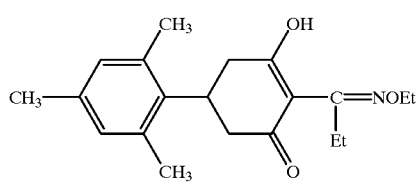
(III)

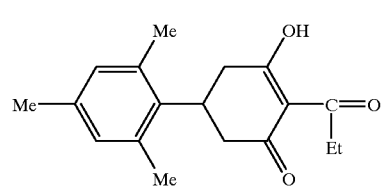
(IV)

What is claimed is:

1. A process of preparing the compound of formula (I):

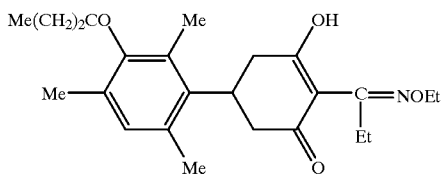
(I)

which comprises a) reacting butyryl chloride with the compound of formula (IV):

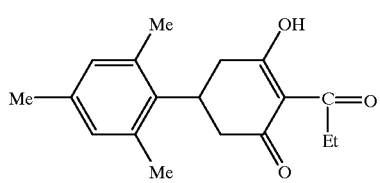
(IV)

in the presence of a Friedel-Crafts catalyst in an inert diluent to produce a compound of formula (II):

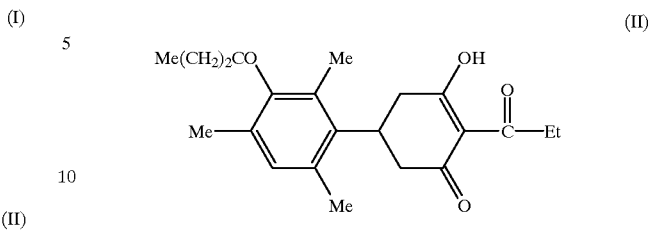
(II)

and b) reacting the compound of formula (II) with ethoxyamine.

2. A process as claimed in claim 1 wherein the Friedel-Crafts catalyst is aluminium chloride.

3. A process as claimed in claim 1 wherein the diluent is an aliphatic or alicyclic hydrocarbon, or a chlorinated aliphatic hydrocarbon.

4. A process as defined in claim 2, wherein the diluent is an aliphatic or alicyclic hydrocarbon, or a chlorinated aliphatic hydrocarbon.

5. A method of preparing a compound of Formula (II), comprising the step of reacting butyryl chloride with a compound of Formula (IV) in the presence of a Friedel-Crafts catalyst in an inert diluent:

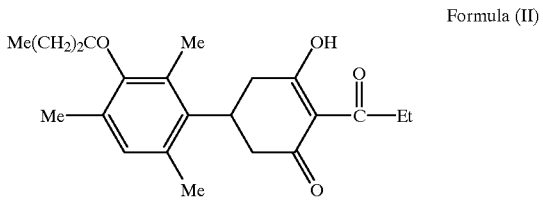
Formula (II)

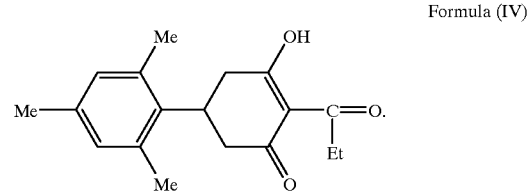
Formula (IV)

6. The method as defined in claim 5, wherein the Friedel-Crafts catalyst comprises aluminum chloride.

7. The method as defined in claim 5, wherein the diluent is one selected from the group consisting of aliphatic hydrocarbons, alicyclic hydrocarbons, and chlorinated aliphatic hydrocarbons.

8. The method as defined in claim 6, wherein the diluent is one selected from the group consisting of aliphatic hydrocarbons, alicyclic hydrocarbons, and chlorinated aliphatic hydrocarbons.

* * * * *